(12) United States Patent
Shepard et al.

(10) Patent No.: US 8,217,219 B2
(45) Date of Patent: Jul. 10, 2012

(54) ANATOMICALLY CONFORMING VAGINAL INSERT

(75) Inventors: Kristin M. Shepard, Appleton, WI (US); MaryAnn Zunker, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1307 days.

(21) Appl. No.: 10/747,420

(22) Filed: Dec. 29, 2003

(65) Prior Publication Data

US 2005/0148995 A1 Jul. 7, 2005

(51) Int. Cl.
*A61F 13/20* (2006.01)

(52) U.S. Cl. .................. 604/364; 604/385.18; 604/288; 606/193; 424/433

(58) Field of Classification Search ............. 604/385.18, 604/904, 364, 288; 606/193; 424/433
See application file for complete search history.

(56) References Cited

U.S. PATENT DOCUMENTS

| | | |
|---|---|---|
| 3,545,439 A | 12/1970 | Duncan |
| 3,783,872 A | 1/1974 | King |
| 3,805,767 A | 4/1974 | Erb |
| 3,920,805 A | 11/1975 | Roseman |
| 3,921,636 A * | 11/1975 | Zaffaroni ................ 424/432 |
| 3,952,347 A | 4/1976 | Comerford et al. |
| 3,967,618 A | 7/1976 | Zaffaroni |
| 3,993,551 A | 11/1976 | Assarsson et al. |
| 3,995,633 A | 12/1976 | Gougeon |
| RE29,207 E | 5/1977 | Bolduc et al. |
| 4,028,290 A | 6/1977 | Reid |
| RE29,345 E | 8/1977 | Erb |
| 4,119,098 A | 10/1978 | Bolduc et al. |
| 4,160,446 A | 7/1979 | Barrington |
| 4,172,066 A | 10/1979 | Zweigle et al. |
| 4,185,618 A | 1/1980 | Corey |
| 4,410,571 A | 10/1983 | Korpman |
| 4,454,055 A | 6/1984 | Richman et al. |
| 4,455,691 A | 6/1984 | Van Aken Redinger et al. |
| 4,509,504 A | 4/1985 | Brundin |
| 4,526,578 A | 7/1985 | Wong |
| 4,534,767 A | 8/1985 | Habib |
| 4,564,362 A | 1/1986 | Burnhill |

(Continued)

FOREIGN PATENT DOCUMENTS

WO WO 95/26455 A1 10/1995

(Continued)

OTHER PUBLICATIONS

Bhatia et al., "Urodynamic effects of a vaginal pessary in women with stress urinary incontinence", *American Journal of Obstetrics and Gynecology*, vol. 147, No. 8, Dec. 15, 1983, pp. 876-884.

(Continued)

*Primary Examiner* — Lynne Anderson
(74) *Attorney, Agent, or Firm* — David J. Arteman; Randall W. Fieldhack

(57) ABSTRACT

A vaginal insert formed from a composition that, prior to introduction to the vagina, has the physical properties of a liquid, semi-soft gel, paste, foam, or viscous material so that it can be effectively delivered to the vaginal canal. After introduction into the vagina, the composition will expand and/or solidify into a semi-solid or solid structure to substantially fill the entire "H" shaped space of the vagina and a portion of the rugal folds along the length of the vaginal canal. Upon solidifying, the composition defines an insert that, in one embodiment, is suitable for use as a tampon and, in another embodiment, is suitable for use as an incontinence device.

16 Claims, 1 Drawing Sheet

U.S. PATENT DOCUMENTS

| | | | |
|---|---|---|---|
| 4,578,065 A | 3/1986 | Habib | |
| 4,601,698 A | 7/1986 | Moulding, Jr. | |
| 4,621,029 A | 11/1986 | Kawaguchi | |
| 4,690,677 A | 9/1987 | Erb | |
| 4,722,595 A | 2/1988 | Siol | |
| 4,846,819 A | 7/1989 | Welch | |
| 4,861,539 A | 8/1989 | Allen et al. | |
| 4,959,216 A | 9/1990 | Daunter | |
| 5,044,376 A | 9/1991 | Shields | |
| 5,065,751 A | 11/1991 | Wolf | |
| 5,090,424 A * | 2/1992 | Simon et al. | 128/885 |
| 5,164,421 A | 11/1992 | Kiamil et al. | |
| 5,224,493 A | 7/1993 | Sawan et al. | |
| 5,236,965 A | 8/1993 | Engelhardt et al. | |
| 5,520,672 A | 5/1996 | Urry | |
| 5,576,364 A | 11/1996 | Isaac et al. | |
| 5,700,553 A | 12/1997 | Cohen et al. | |
| 5,722,931 A | 3/1998 | Heaven | |
| 5,770,528 A | 6/1998 | Mumick | |
| 5,778,886 A | 7/1998 | Shihata | |
| 5,816,248 A | 10/1998 | Anderson et al. | |
| 5,896,982 A | 4/1999 | Surcin et al. | |
| 5,988,169 A | 11/1999 | Anderson et al. | |
| 5,989,580 A | 11/1999 | Wallace et al. | |
| 6,086,909 A | 7/2000 | Harrison | |
| 6,090,038 A | 7/2000 | Zunker et al. | |
| 6,125,850 A | 10/2000 | Sokal et al. | |
| 6,142,928 A | 11/2000 | Zunker et al. | |
| 6,155,259 A | 12/2000 | Conte et al. | |
| 6,216,697 B1 | 4/2001 | Moench et al. | |
| 6,277,768 B1 | 8/2001 | Mumick et al. | |
| 6,302,108 B1 | 10/2001 | Levine | |
| 6,328,991 B1 | 12/2001 | Myhling | |
| 6,332,878 B1 | 12/2001 | Wray et al. | |
| 6,495,080 B1 | 12/2002 | Tsai et al. | |
| 6,503,190 B1 | 1/2003 | Ulmsten et al. | |
| 6,586,529 B2 | 7/2003 | Mumick et al. | |
| 6,602,950 B1 | 8/2003 | Dentler et al. | |
| 2003/0077307 A1 * | 4/2003 | Klofta et al. | 424/401 |
| 2003/0120224 A1 | 6/2003 | Geiser | |
| 2003/0153864 A1 | 8/2003 | Chaffringeon | |

FOREIGN PATENT DOCUMENTS

| | | |
|---|---|---|
| WO | WO 03/017972 A2 | 3/2003 |
| WO | WO 03/032875 | 4/2003 |

OTHER PUBLICATIONS

Nygaard et al., "Exercise and Incontinence", *Obstetrics & Gynecology*, vol. 75, No. 5, May 1990, pp. 848-851.

Nygaard, Ingrid M.D., "Prevention of Exercise Incontinence with Mechanical Devices", *Journal of Reproductive Medicine*, vol. 40, No. 2, Feb. 1995, pp. 89-94.

International Search Report, dated May 12, 2005.

International Preliminary Examination Report, dated Jul. 3, 2006.

\* cited by examiner

ANATOMICALLY CONFORMING VAGINAL INSERT

BACKGROUND OF THE INVENTION

The present invention relates to a composition, device, and a method of delivery for an anatomically conforming vaginal insert.

There have been numerous devices developed to address issues of urinary incontinence and menstruation. Many of these devices are generally round, rectangular, or ovoid in shape. However, the vagina is a hollow fibro-muscular, non-cylindrical tube in which the right and left lateral walls form what resembles an "H" shape with the anterior and posterior walls collapsed upon each other. Additionally, the surface of the vagina is not smooth, there are small ridges on the inner surface of the vagina that extend laterally and upward from the columna rugarum (the long ridges on the anterior and posterior walls). Therefore, while the above devices are successful, it is believed that they could be improved to better take into consideration the shape and internal structures of the vagina.

The present invention addresses that need.

BRIEF SUMMARY OF THE INVENTION

In accordance with the present invention, therefore, an anatomically conforming vaginal insert is provided. The insert is desirably flushable, discardable, or biodegradable and is also biocompatible and suitable for placement in the human body. The insert is a composition that, prior to introduction into the vagina, has the physical properties of a liquid, semi-soft liquid, gel, paste, foam, or viscous material so that it can be easily and effectively delivered into the vaginal canal. After the material has been introduced into the vaginal canal, the composition will expand into a portion of the rugal folds and make intimate contact with a portion the rugae where the consistency of the material will increase in solidity, forming a semi-solid or solid structure to substantially fill the entire "H" shaped space of the vagina within a portion of the vaginal canal. The intimate contact with the rugae ensures that the device will be securely held in place and additionally will not allow the passage of bodily fluids from the uterus or the urethra. Upon solidifying, the composition defines an insert that, in one embodiment, is suitable for use as a tampon and, in another embodiment, is suitable for use as a continence restoration device.

The composition can be delivered to the vagina by any suitable method including an aerosol, squeeze tube, pump or other applicators (known in the art) to which a nozzle is attached or a part of the container. Additionally a suppository, capsule, effervescent or foam producing tablet could also be used to deliver the material into the vaginal canal.

As noted above, in one embodiment, the insert can be used as a continence restoring device, to provide physical support to the bladder neck region by restoring it to normal anatomical position. Because the device substantially fills the entire "H" shaped space of the vagina within a significant portion of the vaginal canal, the device will also act as a backdrop to support the weakened musculature around the bladder neck and urethra to prevent or substantially reduce leakage. In addition, the insert will close off the urethra when increased abdominal pressure occurs, for example, upon coughing, laughing, exercising, lifting, or sneezing but does not interfere with the voluntary release of urine (micturation).

In this embodiment, the composition is non-absorbent and desirably hydrophobic. The composition includes a material selected from polyurethane, silicone, temperature sensitive polymeric materials, ion sensitive polymeric materials, humidity activated materials having a shape memory.

In another embodiment, the insert is contemplated as a catamenial device. In this embodiment, the insert attracts and/or holds menstrual fluids. The composition forming the insert can be hydrophilic so long as the insert can attract and/or hold the menstrual fluid within the interstitial spaces of the material and prevent leaks.

In this embodiment, the composition includes open-cell polyurethane foams, a multi-component reverse thermo-sensitive polymeric system such as that shown and described in PCT publication WO 03/017972, the contents of which are incorporated by reference, a fibrous absorbent structure resembling an open cell polymeric foam such as that shown and described in U.S. Pat. No. 6,261,679 the contents of which are incorporated herein by reference.

DETAILED DESCRIPTION OF THE INVENTION

Figure 1:
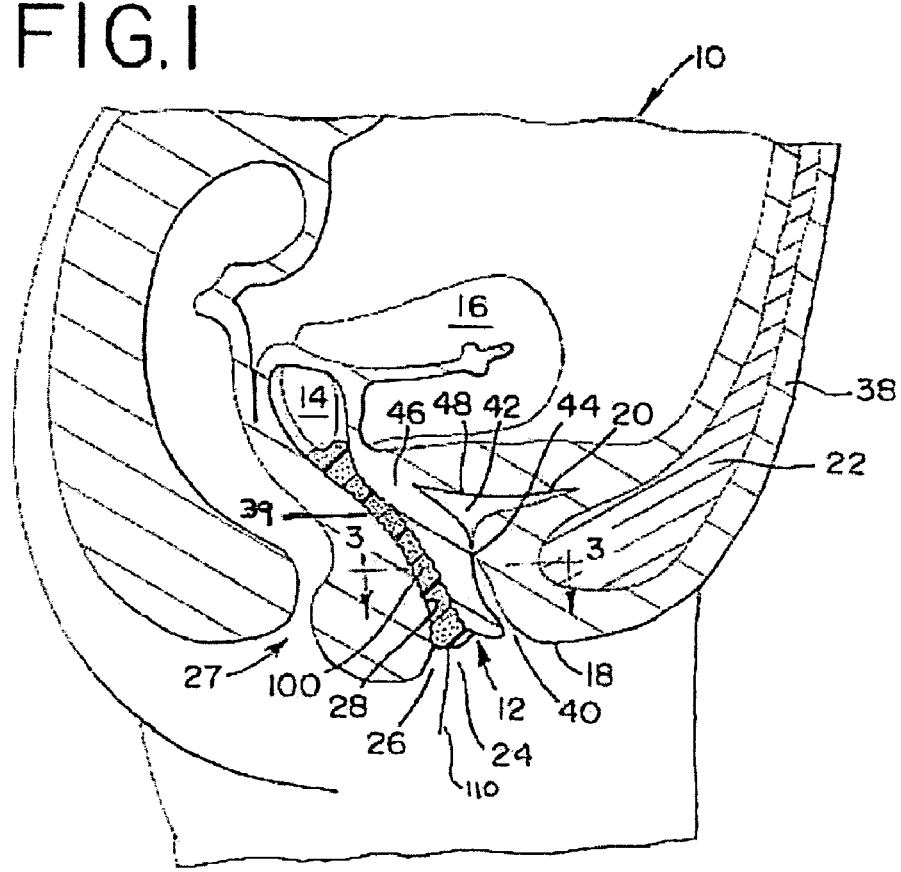
FIG. 1 is a mid-sagittal section of a human torso showing one embodiment of the material of the present invention deposited in the vaginal canal and acting as an incontinence device. The material fills the entire vaginal cavity and numerous rugae allowing restoration to nearly normal anatomical position furthermore, by cooperating with the symphysis pubis to allow the urethral tube to be compressed upon itself and alleviate urinary incontinence during episodes of increased intra-abdominal pressure.

Turning now to FIG. 1, a human torso 10 of a female is shown with a vagina 12, a cervix 14, a uterus 16, a urethra 18, a bladder 20 and a symphysis pubis 22. The vagina 12 has an introital opening 24 that exits the human body 10 that contains a vaginal canal 26 that extends from the introital opening 24 to the cervix 14. The vaginal canal 26 has a length that ranges from between about 4 inches to about 6 inches (about 102 millimeters (mm), to about 153 mm) in most women. The cervix 14 is the entrance to the womb and is located between the upper aspect of the vaginal canal 26 and the uterus 16. The rectum 27 is located posterior to the vagina 12. The vaginal canal 26 has an inner periphery 28.

Figure 2:
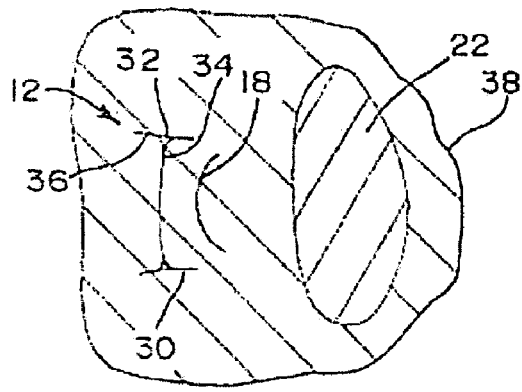
FIG. 2 is a sectional view taken along line 2-2 of FIG. 1 with the material of the present invention not present within the vaginal cavity.
Figure 3:
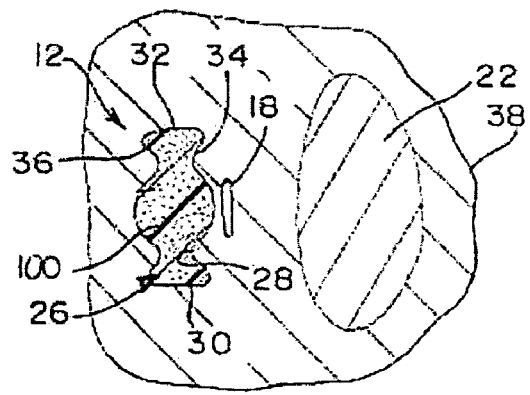
FIG. 3 is the same sectional view of FIG. 2, except that the material of the present invention is present within a portion of the vaginal cavity.

As best seen in FIGS. 2 and 3, the inner periphery 28 is made up of a right lateral wall 30, a left lateral wall 32, an anterior wall 34, and a posterior wall 36. The four walls 30, 32, 34, and 36 generally define an H-shape and encompass the entire 360 degrees of the inner periphery 28. The inner periphery consists of rugal folds 39. The anterior wall 34 is located closest to the urethra 18 and the urethra 18 is located between the symphysis pubis 22 and the vagina 12.

The vaginal canal 26 can be divided into three approximately equal sections, each representing about one-third of the overall length. Each section is approximately 2 inches (approximately 51 mm) in length. The middle third of the vaginal canal 26 is typically the most important section for alleviating female urinary incontinence because of its proximity to the urethra 18. However, in the invention, the material fills the entire length of the vagina and a penetrates into a portion of the rugal folds along its length making positioning in the middle third unimportant. The middle third of the vaginal canal 26 is also horizontally offset from the symphysis pubis 22, which is a bony prominence situated adjacent to a front portion 38 of the human torso 10. Cooperation between a urinary incontinence device positioned along the length of the vagina 12 and the symphysis pubis 22 further allows the urethra 18 to be compressed upon itself to alleviate involuntary urine flow from the bladder.

The urethra 18, also referred to as the urethral tube, is a hollow, tubular structure that extends from a first opening (urethral meatus) 40 that exits the human body 10 to a second opening 42 situated at the lower surface of the bladder 20. The urethra 18 has a length of about 1.5 inches (about 38 mm) in most women. The urethra functions to discharge urine, which is temporarily stored in the bladder 20, from the human body. The urethra 18 has a plurality of urethral sphincter muscles 44 located along the length of its inner periphery. The urethral sphincter muscles 44 are situated below the opening 42 and are ring like muscles that normally maintain constriction of the urethra 18 to prevent the passage of urine. The relaxation of the urethral sphincter muscles 44 by normal physiological functioning will permit urine to be voluntarily expelled from the body.

Again, referring to FIG. 1, the human torso 10 further includes musculature and body tissue located in the urethrovaginal myofascial area 46 that is situated between the vagina 12 and the symphysis pubis 22. The bladder 20 lies posterior to the symphysis pubis 22 and is separated from the rectum 27 by the vagina 12 and the uterus 16. The ureters (not shown) that transport urine from the kidneys to the bladder 20, pass from the pelvis to the posterior aspect of the urinary bladder 20. The fundus vesicae 48, into which both of the ureters terminate is located adjacent to the anterior wall 34 of the vagina 12.

As shown in FIG. 1, according to one embodiment of the present invention, the composition of the present invention is shown deposited within the vagina 12 and in the form of a urinary incontinence device 100 positioned in the vaginal canal 26. The urinary incontinence device 100 is designed to bridge across and along the length of the vagina 12 to support the musculature and body tissue located in the urethra-vaginal myofascial area 46. It will be understood from the following description that the incontinence device will substantially fill the entire lateral 360 degree originally H-shaped space of the vagina 12 along the entire length of the vaginal canal 26.

FIG. 3 shows the device, by virtue of its placement and composition, acting as an incontinence device 100. It will be noted that the device substantially fills the entire space of the vagina 12 providing a supportive backdrop for the urethral tube 18. The urethral tube 18 can now be sufficiently compressed during increased intra-abdominal pressure periods thereby intercepting the flow of urine and also to provide support to the urinary sphincter muscle 44 so that it can function properly. By permitting the urethral tube 18 to be compressed upon itself between the urinary incontinence device 100 and the symphysis pubis 22, the involuntary flow of urine from the bladder is limited.

As noted above, the composition of the present invention can be chosen to provide a urinary incontinence insert or to provide a catamenial insert. The composition desirably is a low surface tension material that will allow uniform expansion under relatively low pressure. As a result, the composition will expand then solidify when present in the vaginal canal and will conform to the shape of the vagina, penetrating a portion of the folds of the mucous membrane (ruga) of the walls 30, 32, 34, and 36. The composition will substantially or effectively seal a portion of the vaginal canal. In this regard, the composition includes a material selected from polyurethane, silicone, a hydrogel, temperature sensitive polymeric materials, ion sensitive materials, bioelastic polypeptide polymers, a multi-component reverse thermo-sensitive polymeric system such as that shown and described in PCT publication WO 03/017972, the contents of which are incorporated by reference, a fibrous absorbent structure resembling an open cell polymeric foam such as that shown and described in U.S. Pat. No. 6,261,679 the contents of which are incorporated herein by reference.

The polyurethane material may be an elastomeric or foam material than can be prepared using a relatively low amount of water. A possible polyurethane material is described in U.S. Pat. No. 5,164,421, the contents of which are incorporated herein by reference.

A silicon composition may include a medical grade silicone elastomer. In this embodiment, the uncured silicone elastomer in a fluid state is blended with a catalyst for solidifying the elastomer and a dilution fluid to control the viscosity during delivery and to control the modulus of elasticity of the cured solidified material. The silicone elastomer is self-curing and, upon curing has a modulus of elasticity that is substantially the same as the vagina so that the insert, upon solidifying remains resilient, can act as a physical support yet not cause discomfort.

The silicone may also include an organosilicon rubber, desirably a foamable polymer where the foam comprises a resilient, semi-rigid, closed-cell foam.

The composition of the present invention may also include a hydrogel. The term "hydrogel" as used in the specification refers to water-containing gels. These materials, when contacted with a body fluid, such as physiological fluids, swell at least 20% in volume. The amount of swelling of the hydrogel material in contact with the body fluid is desirably preferably at least 40%, more desirably at least 80% and may well be in the range between 20 and 300% depending on the material used, amount of fluid to which the device is exposed and the like.

The material should be essentially inert and harmless to the body fluid and surrounding tissues and should remain intact, that is, should not be absorbed by the human or animal body into which the device is inserted. The material in the dry state should be essentially elastic and plastic only to a very small extent. In its unswollen or non-hydrated state it may be rigid, semi-rigid, or stiff, but should preferably soften upon swelling and retain a resilient property.

Suitable hydrogels are polymers and copolymers of the acrylic type such as cross-linked polyacrylamide and polymers and copolymers of acrylic and methacrylic esters having at least one hydroxy radical in the side chain. A preferred monomer is 2-hydroxy-ethyl-methacrylate; other preferred monomers are monometharylic esters of di- or triethylene glycol of 2,3-dihydroxypropane. As cross-linking agents, polyfunctional acrylates, such as the esters of the same glycols, e.g. ethylene glycol-bis-methacrylate, are useful. Materials useful in accordance with the present invention as well as a process for their preparation are described in the U.S. Pat. No. 3,943,045, the disclosure of which is hereby incorporated by reference.

For example, a polymer of vinyl pyrrolidone and nylon in which liquid nylon or bulk nylon is polymerized with vinyl pyrrolidone, the nature of the reaction possibly being a graft polymerization or polymerization followed by cross-linking. The resulting material may be termed a hydrogel. Using such a material, the swelling and the water absorption power may be altered by changing the amounts of nylon and vinyl pyrrolidone to be polymerized. As an example, three (3) parts vinyl pyrrolidone and 1 part nylon forms a polymer having an expansion factor of 1.48, that is, it swells 48% in water, with a water content of 66%; five (5) parts vinyl pyrrolidone and 1 part nylon forms a polymer having an expansion factor of 1.78 with a water content of 78%. Other variations in monomer proportions will produce corresponding changes in the properties of the resulting hydrogel and are easily determined by the skilled worker.

As noted above, the composition may include a temperature sensitive polymeric material. Temperature sensitive polymeric materials are described in PCT WO 98/29501, the entire contents of which are incorporated herein by reference.

The temperature sensitive polymeric materials may be based on modified hydroxypropylcellulose compositions. In particular, it is believed that methylated hydroxypropylcellulose (mHPC) compositions (not methylhydroxypropylcellulose (MHPC), a copolymer of methylcellulose and hydroxypropylcellulose) will be effective for use as the insert of the present invention. These materials are described in U.S. Pat. No. 5,770,528, the entire contents of which are incorporated herein by reference. It is noted that these materials may also be considered an ion sensitive material.

m-HPC is produced by methylation of HPC with methylating agents such as dimethylsulfate or methylchloride. The cloud point of m-HPC can be precisely controlled by the degree of methylation. Unlike HPC which, when precipitated in water, forms a supramolecular helical structure along the backbone leading to a very loose, open precipitate with no gel-like property, m-HPC precipitates as a solid mass with a very low level of hydration. This precipitation behavior may be caused by the introduction of methyl groups, which disrupts the helical structure and increases overall hydrophobicity of the polymer chain. m-HPC has cohesive energy and gel strength comparable to poly(N-isopropylacrylamide) (IPAM), above the triggering point. As used herein the phrase "triggering point" or "trigger temperature" refers to the LCST or cloud point temperature.

LCST polymers are Low Critical Solution Temperature polymers. A LCST polymer has the property of being less soluble at increased temperatures than at lower temperatures. The polymer has a lower critical solution temperature at which significant insolubilization occurs. A LCST polymer may have having a single LCST point. In some circumstances, however, it is appropriate to use a polymer solution which provides two different LCST points, either as a result of including two LCST polymers having different LCST points or as a result of using a polymer having two different LCST points. It will be appreciated that when the polymer or polymer blend provides more than one LCST point there may be two different zones at which insolubilization and/or solubilization occurs or there may be a wide range of conditions at which these effects occur.

LCST polymers and their solution properties are well known and are described in, for instance, Priest et al Chapter 18 in "Reversible polymeric gels and related systems", American Chemical Society, 1987 and in U.S. Pat. Nos. 3,244,640, 3,567,650 and 3,594,326, W092/20771 and JPB-92034983 and JP-B-92034985, JP-A-04139206 and in Galaev and Mattiasson, Enzyme Microb. Technol., 1993, 15, 354-366. Suitable monomers and polymerization techniques are described in U.S. Pat. No. 5,147,923.

The LCST polymer may be a naturally occurring polymer such as certain cellulose derivatives, such as the methyl, hydroxypropyl and mixed methyl/hydroxypropyl cellulose ethers. It is generally preferred that the LCST polymer to be a synthetic polymer formed by polymerization of what can be termed an LCST monomer (or more than one such monomer), optionally as a copolymer with one or more further types of monomer. Suitable LCST monomers include N-alkylacrylamide, N,N-dialkylacrylamide, diacetone acrylamide, N-acryloylpyrrolidine, vinylacetate, certain (meth) acrylate esters (especially hydroxypropyl esters), styrene, and various other vinyl monomers, especially N-vinylimidazoline and the like.

When the LCST polymer is a copolymer with other monomers, the co-monomer is usually hydrophilic and can be non-ionic or ionic. Suitable non-ionic monomers include acrylamide (ACM), substituted acrylamides for instance those with one or two aliphatic N-substituents, some of which, such as N,N-dimethyl acrylamide (NNDMACM), may contribute to LCST properties, hydroxyethyl acrylate, vinylpyrrolidine and hydrolysed vinyl acetate. Anionic or cationic monomer can be used in place of or in addition to the non-ionic co-monomer to form a copolymer or terpolymer respectively with the one or more LCST monomers. Suitable anionic monomers include ethylenically unsaturated carboxylic or sulphonic acid monomers, for example (meth) acrylic acid and alkaline salts thereof, and 2-acrylamido methyl propane sulphonic acid. Suitable cationic monomers include dialkyl amino alkyl(meth)acrylates and acrylamides as acid addition products of quaternary ammonium salts, for example dialkylaminoethyl(meth)acrylate acid addition salts.

Diacetone acrylamide (DMM), N,N-dimethyl acrylamide (NNDMACM), N-isopropyl acrylamide (NIPA) and N-hydroxypropyl acrylamide are particularly useful LCST monomers. LCST polymers that may be used include DAAM/ACM copolymers, NNDMACM/NIPA copolymers, NNDMACM/ACM copolymers, NIPA/ACM copolymers and poly-N-isopropylacrylamide (poly-NIPA) homopolymer.

Ion sensitive polymers are described in U.S. Pat. No. 6,602,955, the contents of which are incorporated herein by reference.

It is noted above that bioelastic polymers may be useful as the composition of the present invention. Bioelastic polymers are described in U.S. Pat. No. 5,520,672, the contents of which are incorporated herein by reference. The bioelastic polymers are capable from changing from a condensed to a swollen state upon contact with a pre-selected physiological condition (such as temperature or salt content) so that the inverse temperature transition point of the bioelastomer is selectively located either above or below the ambient temperature of the local environment in which the bioelastomer is found; this allows selective unfolding and disassembly of polymer matrices to favor absorbency or brings about a contraction that causes the hydrophobic properties of the elastomers to take precedence.

The bioelastic polymers may include elastomeric units selected from the group consisting of bioelastic pentapeptides, tetrapeptides, and nonapeptides. By selecting the side changes present in the polymer portion of the composition, control is possible over the absorbence properties of the composition including the ability to the absorbent to retain absorbed liquid under stresses and external pressures. Proper selection of hydrophobic (apolar) and polar residues, which is known by one skilled in the art, will provide the resulting polymer with the property such that it is soluble in water at low temperatures but as the temperature is raised through a transitional range, they aggregate into condensed, more-ordered states.

The above materials should be selected such that the temperature at which they form into a semi-solid material should be greater than the temperature at which they do not have a semi-solid form. Desirably, the temperature at which they form into a semi-solid material is from about 35° to about 39° C., more desirably about 37° C. The temperature at which the material can be delivered to the vaginal canal is from about 16° to about 27° C., desirably about 20° C.

With respect to each of the above materials, one skilled in the art can select the appropriate material and/or modify the above material to render it more hydrophobic or more hydrophilic depending on the end use of the insert that is formed from the composition. For example, where the insert is to be used as an incontinence insert, the insert is formed from a composition that is non-absorbent and desirably hydrophobic. On the other hand, where the insert is to be used as a catamenial device, the insert is formed from a composition that is absorbent.

It is also contemplated that a withdrawal device 110 may be provided with the composition such that upon delivery of the composition to the vaginal canal, the withdrawal device 110 may also be delivered to the vaginal canal so that as the composition solidifies, the withdrawal device 110 is secured within the insert formed as a result of the solidification of the composition.

The composition including one of more of the materials described above is contained in a delivery device that will contain the composition until delivery to the vaginal canal. The delivery device can include, but is not limited to an aerosol, squeeze tube, pump or other applicators (known in the art) to which a nozzle is attached or part of the container. Additionally a suppository, capsule, effervescent or foam producing tablet or other suitable device to deliver the composition into the vaginal canal where upon introduction, the composition will solidify to a semi-solid or solid form having elasticity and resiliency.

The present invention therefore contemplates a method of providing a vaginal insert that includes providing a delivery device that contains a composition and dispensing the composition to the vaginal canal where the composition is fluid like when outside the vagina but that upon contact with the interior surface of the vaginal canal and rugae will solidify to form a malleable, resilient insert suitable for use as an incontinence insert or catamenial insert depending upon the properties of the composition and independent of the location of the insert.

While the invention has been described in conjunction with specific embodiments it is to be understood that many alternatives, modifications, and variations will be apparent to those skilled in the art in light of the foregoing detailed description. It is therefore intended that the foregoing description be regarded as illustrative rather than limiting, and that it be understood that it is the following claims, including all equivalents, that are intended to define the spirit and scope of this invention.

What is claimed:

1. An anatomically conforming vaginal insert formed from a composition wherein the composition includes a material which is introduced into a vaginal canal as a viscous material at a first temperature and after insertion into the vaginal canal becomes a semi-solid at a second temperature greater than the first temperature, wherein the first temperature is about 20° C. and the material has increased solidity at the second temperature as compared to the first temperature.

2. The vaginal insert of claim 1 wherein the composition is selected from the group consisting of a material selected from polyurethane, silicone, a hydrogel, temperature sensitive polymeric materials, ion sensitive materials, bioelastic polypeptide polymers, a multi-component reverse thermosensitive polymeric system, and a fibrous absorbent structure resembling an open cell polymeric foam.

3. The vaginal insert of claim 2 wherein the material is a temperature sensitive polymeric material having a low critical solution temperature such that the second temperature is about 37° C.

4. The vaginal insert of claim 1 wherein the insert is hydrophobic.

5. The vaginal insert of claim 4 wherein the vaginal insert is an incontinence insert.

6. The vaginal insert of claim 5 wherein the vaginal insert supports musculature around a bladder neck.

7. The vaginal insert of claim 1 wherein the composition expands upon contact with the vaginal canal.

8. The vaginal insert of claim 7 wherein upon expansion, the insert substantially fills an entire lateral portion of the vaginal canal.

9. The vaginal insert of claim 1 wherein the material is a polymer having lower solubility at the second temperature than the first temperature.

10. The vaginal insert of claim 1 wherein the material is a liquid, semi-soft liquid, gel, paste, foam or other viscous material at a temperature of about 16° to about 27° C., but forms a semi-solid material at a temperature of about 35° to about 39° C.

11. The vaginal insert of claim 1 wherein the insert is non-absorbent.

12. The vaginal insert of claim 11 wherein the material is selected from the group consisting of a material selected from polyurethane, silicone, temperature sensitive polymeric materials, ion sensitive polymeric materials, and humidity activated materials having a shape memory.

13. The vaginal insert of claim 1 wherein the material is adapted to function as a tampon or continence restoration device.

14. The vaginal insert of claim 1, wherein the vaginal insert is formulated with a withdrawal device, so that when the material solidifies after entering the body, the withdrawal device is secured within the insert as a result of the material solidifying.

15. An anatomically conforming vaginal insert formed from a composition that is introduced into a vaginal canal as a liquid, semi-soft liquid, gel, paste, foam or viscous composition at a temperature of about 16° to about 27° C., and after insertion into the vaginal canal becomes a solid or semi-solid material at a temperature of about 35° to about 39° C., wherein the vaginal insert is formulated with a withdrawal device, so that when the composition solidifies, the withdrawal device is secured within the insert as a result of the composition solidifying.

16. The vaginal insert of claim 15 wherein the composition is adapted for use as a tampon or continence restoration device.

* * * * *